(12) United States Patent
Chakravarthy et al.

(10) Patent No.: US 8,473,047 B2
(45) Date of Patent: Jun. 25, 2013

(54) MULTIFREQUENCY BIOIMPEDENCE DEVICE AND RELATED METHODS

(75) Inventors: Niranjan Chakravarthy, Eden Prairie, MN (US); Rodolphe Katra, Blaine, MN (US); Imad Libbus, St. Paul, MN (US)

(73) Assignee: Corventis, Inc., San Jose, CA (US)

( * ) Notice: Subject to any disclaimer, the term of this patent is extended or adjusted under 35 U.S.C. 154(b) by 330 days.

(21) Appl. No.: 12/878,886

(22) Filed: Sep. 9, 2010

(65) Prior Publication Data
US 2012/0035494 A1 Feb. 9, 2012

Related U.S. Application Data

(60) Provisional application No. 61/379,651, filed on Sep. 2, 2010, provisional application No. 61/370,345, filed on Aug. 3, 2010.

(51) Int. Cl.
*A61B 5/05* (2006.01)
(52) U.S. Cl.
USPC .......................................................... 600/547
(58) Field of Classification Search
USPC .......................................................... 600/547
See application file for complete search history.

(56) References Cited

U.S. PATENT DOCUMENTS

| 7,177,681 B2 | 2/2007 | Zhu et al. |
| 7,400,920 B1 | 7/2008 | Gill et al. |
| 7,647,101 B2 | 1/2010 | Libbus et al. |
| 2005/0101875 A1* | 5/2005 | Semler et al. .................. 600/509 |
| 2005/0177060 A1* | 8/2005 | Yamazaki et al. ............. 600/547 |
| 2007/0175827 A1 | 8/2007 | Wariar |
| 2010/0168530 A1* | 7/2010 | Chetham et al. .............. 600/301 |
| 2012/0035432 A1 | 2/2012 | Katra et al. |

FOREIGN PATENT DOCUMENTS

| WO | 2009/036313 A1 | 3/2009 |
| WO | 2009/036321 A1 | 3/2009 |
| WO | 2009/036327 A1 | 3/2009 |
| WO | 2009/036329 A1 | 3/2009 |
| WO | 2009/036369 A1 | 3/2009 |

OTHER PUBLICATIONS

Cianci, R., et al. Body fluid compartments in hypertension. European Review for Medical and Pharmacological Sciences 2006, 10, pp. 75-78.
Yu, C-M., et al. Intrathoracic Impedance Monitoring in Patients With Heart Failure. Circulation 2005, 112, pp. 841-848.
Kyle, U.G., et al. Bioelectrical impedance analysis-part I: Review of principles and methods. Clinical Nutrition 2004, 23, pp. 1226-1243.

* cited by examiner

*Primary Examiner* — Max Hindenburg
*Assistant Examiner* — Renee Danega
(74) *Attorney, Agent, or Firm* — Billion & Armitage; Benjamin C. Armitage

(57) ABSTRACT

Embodiments relate to a device and a method of monitoring and analyzing physiological parameters of a patient. The method includes electrically connecting one or more electrodes with a measurement site of a patient, generating a stimulation signal or signals sufficient to provide multiple stimulation frequencies, multiple waveforms or a combination thereof, measuring a one or more bioimpedance values from the generated signals and analyzing at least one of a fluid bioimpedance contribution, fat bioimpedance contribution or ion bioimpedance contribution within the one or more bioimpedance values sufficient to generate a physiological report.

20 Claims, 7 Drawing Sheets

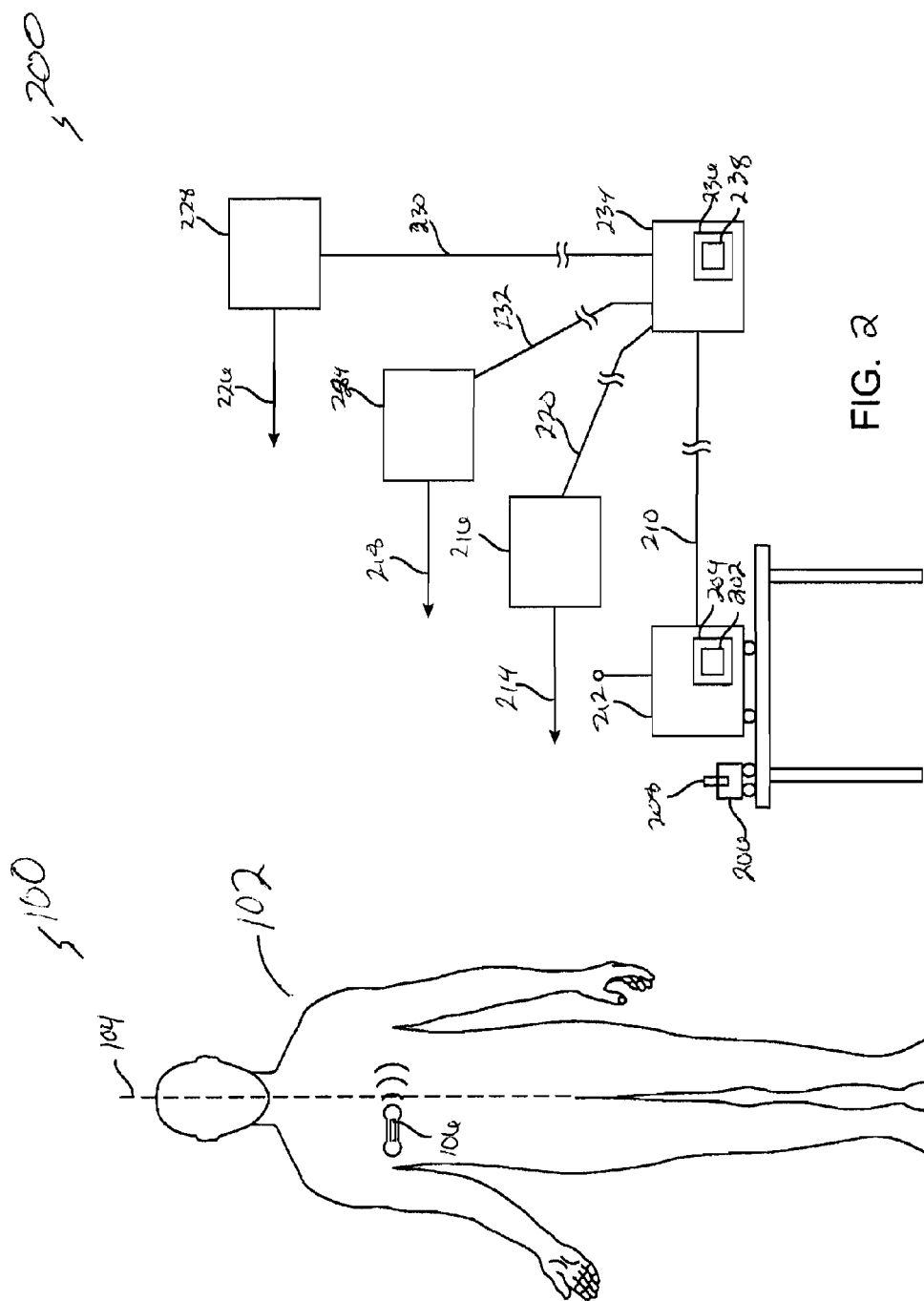

MULTIFREQUENCY BIOIMPEDENCE DEVICE AND RELATED METHODS

CROSS-REFERENCE TO RELATED APPLICATIONS

The present application is related to and claims benefit of US Provisional Patent Application No. 61/370,345; titled MEDICAL DEVICE AND METHODS OF MONITORING A PATIENT WITH RENAL DYSFUNCTION; and filed 3 Aug. 2010, which is hereby incorporated by reference for any purpose; and the present application is related to and claims benefit of US Provisional Patent Application No. 61/379,651; titled MULTIFREQUENCY BIOIMPEDANCE DEVICE AND RELATED METHODS; and filed 2 Sep. 2010.

BACKGROUND

Weight, body fluid bioimpedance values and other physiological parameters have been used in the past to attempt to identify and track heart failure status in a patient. Such measures are often confounded or disguised by changing fat and fluid content, both of which can vary significantly in one patient and across a sampling of patient data. Measurements are often only made during periods of hospitalization or physiological instability, which may render such measurements unreliable. For example, weight measurements may be unreliable due to a high fluid content in a patient or elevated interstitial fat content and adipose tissues levels. Such factors affect a patient's normal baseline measurements, the tracking of heart failure status and the quantification of the difference of a specific patient's fluid levels as compared to a normal patient data or similarly conditioned patient data set.

If monitoring a patient's physiological conditions outside of a hospital setting, the devices utilized are often painful or uncomfortable for a patient to use and take measurements with. Such intrusive devices and methods may lead to poor patient compliance. It is often difficult or not practical for a doctor to monitor a patient's health status or heart failure status remotely or to have access to long term measurements of a number of physiological parameters. Additionally, temporal measurements monitored within a patient may be susceptible to chronically changing proportions of fat and fluid that may mask the underlying deterioration in patient health status.

SUMMARY

Embodiments relate to a medical device including a measuring interface located between a device and a measuring site of a patient, one or more electrodes to generate multiple stimulation frequencies, multiple waveforms or a combination thereof, positioned at the measuring interface and in electrical contact with a portion of the patient. The device also includes circuitry to measure fluid bioimpedance, fat bioimpedance or a combination thereof, as a result of the generated multiple stimulation frequencies, multiple waveforms or a combination thereof from the one or more electrodes and a processor system to isolate a fluid contribution and a fat contribution from a total bioimpedance value from which a physiological report can be generated.

Embodiments further describe a method of monitoring and analyzing physiological parameters of a patient. The method includes connecting one or more electrodes with a measurement site of a patient, generating an electrical stimulation signal or signals sufficient to provide multiple stimulation frequencies, multiple waveforms or a combination thereof, measuring one or more bioimpedance values from the generated signals and analyzing at least one of fluid bioimpedance contribution, fat bioimpedance contribution or ion bioimpedance contribution within the one or more bioimpedance values sufficient to generate a physiological report.

BRIEF DESCRIPTION OF THE DRAWINGS

The accompanying drawings illustrate non-limiting example embodiments of the invention.

FIG. 1 illustrates a schematic view of a patient utilizing a medical device measuring one or more bioimpedance values, according to some embodiments.

FIG. 2 illustrates a schematic view of monitoring and treatment system, according to some embodiments.

DETAILED DESCRIPTION

Figure 3:
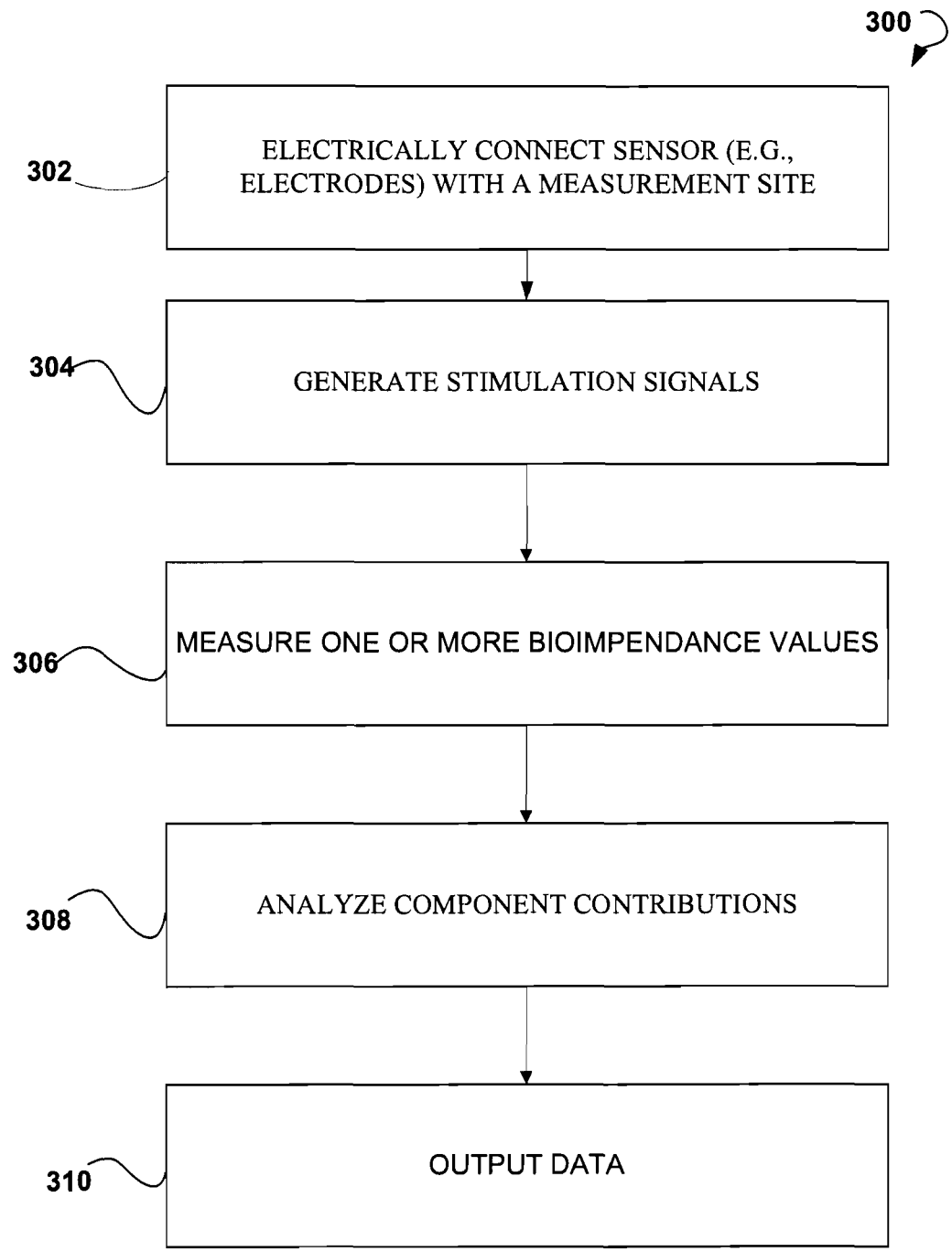
FIG. 3 illustrates a block flow diagram of a method of monitoring and analyzing physiological conditions within a patient, according to some embodiments.

Throughout the following description, specific details are set forth in order to provide a more thorough understanding of the invention. However, the invention may be practiced without these particulars. In other instances, well known elements have not been shown or described in detail in order to avoid unnecessarily obscuring the invention. The drawings show, by way of illustration, specific embodiments in which the invention may be practiced. These embodiments may be combined, other elements may be utilized or structural or logical changes may be made without departing from the scope of the invention. Accordingly, the specification and drawings are to be regarded in an illustrative, rather than a restrictive, sense.

All publications, patents and patent documents referred to in this document are incorporated by reference herein in their entirety, as though individually incorporated by reference. In the event of inconsistent usages between this document and those documents so incorporated by reference, the usage in the incorporated references should be considered supplementary to that of this document; for irreconcilable inconsistencies, the usage in this document controls. Reference is made to a co-pending, co-assigned patent application titled "MEDICAL DEVICE AND METHODS OF MONITORING A PATIENT WITH RENAL DYSFUNCTION"assigned U.S. patent application Ser. No. 12/878,873. Applicant further makes reference to application no. PCT/US2008076288, now published as WO 2009/036369, and incorporates same by reference for any purpose.

In this document, the terms "a" or "an" are used, as is common in patent documents, to include one or more than one, independent of any other instances or usages of "at least one" or "one or more". In this document, the term "or" is used to refer to a nonexclusive or, such that "A, B or C" includes "A only", "B only", "C only", "A and B", "B and C", "A and C", and "A, B and C", unless otherwise indicated. The terms "above" and "below" are used to describe two different directions in relation to the center of a composite and the terms "upper" and "lower" may be used to describe two different surfaces of a composite. However, these terms are used merely for ease of description and are not to be understood as fixing the orientation of the described embodiments. In the appended aspects or claims, the terms "first", "second" and "third", etc. are used merely as labels, and are not intended to impose numerical requirements on their objects.

Embodiments of the present invention relate to a multi-stimulation, e.g., multifrequency or multi-signal or multi-amplitude, bioimpedance medical device and methods for measuring physiological parameters using the same. The device and method described in the present embodiments relate to the utilization of multiple stimulation frequencies, waveforms or both, to measure one or more physiological parameters of a patient through bioimpedance. The embodiments may be used for a single or one-time analysis of a patient or, alternatively, may be used to track a patient's change in physiological conditions over time—both while in a health care facility and while outside the health care facility, e.g., at home. The device and methods described are capable of isolating and removing interferent component measurements, leaving reliable, accurate physiological parameter measurements useful for diagnosis and treatment analysis. This quantification of the contribution of such parameters, e.g., fat and/or fluid, can guide physicians and other health care providers in assessing and treating a patient for a variety of conditions, such as heart failure status.

Referring to FIG. 1, a schematic view 100 of a patient utilizing a medical device measuring one or more bioimpedance values is shown, according to some embodiments. A patient 102 may utilize a medical device 106 on either side a midline 104 of the patient, i.e., on one side of the sagittal plane. In one example, the device is on the patient above the mid-transverse plane and in front of the coronal plane. The medical device 106 can be an adherent device on the surface of the skin. In another example, the device 106 is implantable. If implantable, the device may be integrated with medical devices performing other tasks or functions, such as a pacemaker for example. The medical device 106 may be partially implantable in one embodiment. The device 106 may be positioned on or in the patient in many possible positions, so long as one or more electrodes of the device are in electrical contact or connectivity with a portion (i.e., measurement site) of the patient's body capable of providing one or more bioimpedance values when stimulated. The device 106 can further apply stimulation signals to the patient's body. Examples of such portions of the patient's body include skin, fat, tissues, interstitial fluid or blood, among others. Measurement sites may be chosen to minimize interferent signal and maximize the desired component signals. For example, if fat is an interferent, a portion of the body with less fat and more muscle present may be chosen as the measurement site.

Referring to FIG. 2, a schematic view 200 of monitoring and treatment system is shown, according to some embodiments. The device 106 of FIG. 1 may communicate with a remote center 234, located remotely. The remote center 234 may be located within the same room or thousands of miles away from the device 106. The device 106 can communicate wirelessly with an intermediate device 212, such as through the internet or cellular phone system. The intermediate device 212 can communicate directly with the medical device 106 and then relay information to the remote center 234, for example. The medical device 106 and monitoring system can include a distributed processing system, for example. The distributed processing system can include at least one processor located on-board the medical device 106, at least one processor 204 on the intermediate device 212 and at least one processor 236 on the remote center 234, each of which processors is in electronic communication with the other processors. At least one processor 204 includes a tangible medium 202. Processor 236 can include a tangible medium 238, for example. Remote processor 236 can include a backend server located at the remote center 234. Remote center 234 can be in communication with a health care provider 216 with a communication system 220, such as the internet, phone lines, wireless and/or satellite phone, for example. Health care provider 216, such as a family member, can be in communication with the patient 102, for example, with a two way communication system 214, such as by cellular phone, email or landline phone.

Remote center 234 can be in communication with a health care professional 224, such as a physician, with communication system 232. System 232 may include the internet, an intranet, phone lines wireless and/or satellite phone. Health care professional 224 may be in communication with patient 102 with two-way communication system 218. Remote center 234 may be in communication with an emergency responder 228, such as an operator or paramedic, for example, with communications system 230. Responder 228 can travel 226 to the patient 102. Thus, in many embodiments, the monitoring and treatment systems associated with device 106 may form a close communication loop in response to signals from the device 106.

In many embodiments, the device 106 includes a reusable or rechargeable electronics module. One module 208 may be recharged using a charging station 206 while another module is located within the device. In some embodiments, the intermediate device 212 may comprise a charging module, data transfer, storage and/or transmission, such that one of the electronics modules may be placed in the intermediate device for charging and/or data transfer while the other electronics module is worn by the patient.

Referring to FIG. 3, a block flow diagram 300 of a method of monitoring and analyzing a patient is shown, according to some embodiments. One or more electrodes may be electrically connected 302 with a measurement site of a patient. One or more stimulation signals may be generated 304 sufficient to provide multiple stimulation frequencies, multiple waveforms or a combination thereof. One or more bioimpedance values may be measured 306 from the generated signals, for example. At least one of a fluid bioimpedance contribution, fat bioimpedance contribution or ion bioimpedance contribution may be analyzed 308 within the one or more bioimpedance values sufficient to generate a physiological report.

The one or more electrodes may be positioned on or in a medical device. The medical device may be an implant, a partial implant or an adherent device. The bioimpedance medical device may be integrated with one or more other functional devices, such as pacemakers or glucose monitors, for example. The one or more electrodes may electrically connect 302, such as by contacting a portion of a patient that is capable to responding to a stimulation signal (i.e., measurement site). Electrically connect 302 refers to any contact between one or more electrodes and a portion of a patient's body such that an electrical signal may be generated or stimulated.

One or more stimulation signals may be generated 304 sufficient to provide multiple frequencies, multiple waveforms or a combination thereof. The device may generate multiple spot frequencies or a frequency sweep, for example. Spot frequency values may be chosen based on known bioimpedance reactions of certain biological components at a certain measurement site. For example, a signal may be generated at a frequency where fat is known to resist an electrical current and another measurement where fluid is known to interact with the signal. An example of a frequency sweep would be to generate signals at multiple values at set intervals. Signals generated 304 may be between about 5 kHz to about 1000 kHz, between about 100 kHz and about 800 kHz or between about 50 kHz and about 500 kHz, for example. Types of waveforms may include sine, square, triangle, composite, sawtooth signals or a combination thereof.

One or more bioimpedance values may be measured 306 from the generated signals, for example. Measuring 306 may include measuring resistance, reactance or changes in resistance and/or reactance over time, for example. Physiological parameters that may be measured include amounts of fat, fluid, ions, hydration levels, blood flow or combinations thereof, for example.

At least one of a fluid bioimpedance contribution, fat bioimpedance contribution or ion bioimpedance contribution may be analyzed 308 within the one or more bioimpedance values sufficient to generate a physiological report. Analyzing 308 may include identifying, isolating and quantifying individual or group physiological component values. Analyzing 308 may include subtracting measurement signals, combining measurements or isolating measurements for example. Analyzing 308 may include identifying correlations or lack of correlations between physiological component values.

By identifying the contribution of interferent and desirable component measurements from a larger group of signals, a multitude of useful data may be generated. The values determined may be used to establish initial conditions or a baseline for a patient, an endpoint for care or long-term tracking of a patient's health. The data generated may be used to generate a report or display to a physician or patient that instructs or gives guidelines on a course of action, for example. Embodiments of the invention allow for simultaneous temporal tracking of both fluid and fat status, which is critical for monitoring heart failure patients, for example.

A custom monitoring and treatment program may be created based on long term monitoring according to embodiments of the invention. An individual patient's weight, fluid status, fat status and other physiological parameters may be recorded away from a hospital setting and then used by a physician for individual comparison when in treatment or monitored remotely.

As mentioned previously, frequency sweeps may be utilized to quantify the contribution of non-fluid parameters, such as fat, ions or other components, to derive fluid-specific values for long-term tracking. The method allows for an identification of whether a signal and result are reliable, based on the identification of other components. For example, a high ion measurement may indicate the need to re-measure a patient's fluid status. Spot recording of physiological components may be accomplished by adapting a stimulation waveform to obtain a fluid bioimpedance value. Adapting may include changing a signal's amplitude, frequency or shape, for example. Adapting may reduce the number of false positives, for example.

Figure 4:
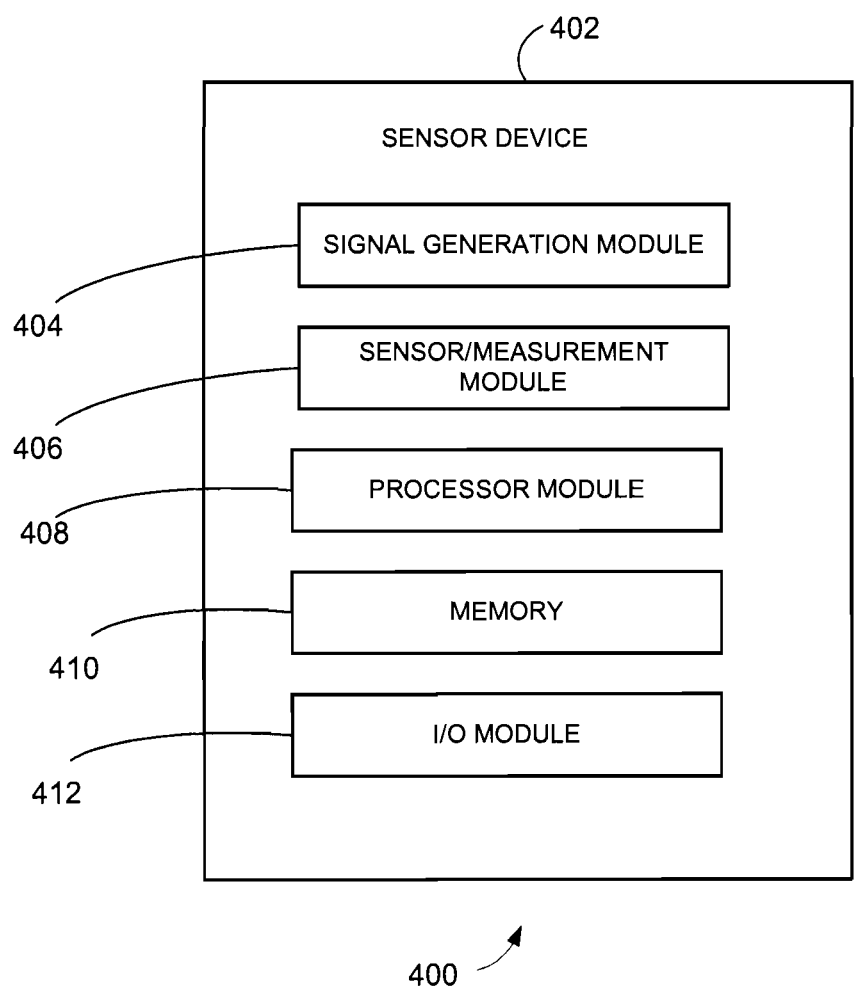
FIG. 4 illustrates a schematic view of a medical device and monitoring system, according to some embodiments.

Referring to FIG. 4, a schematic view 400 of a medical device and monitoring system, according to some embodiments. A device or system 402 may include a signal generation module 404, sensor/measurement module 406, processor module 408, memory 410 and input/output module 412. The modules shown may be some combination of hardware, software or integrated hardware and software, for example.

Figure 5:
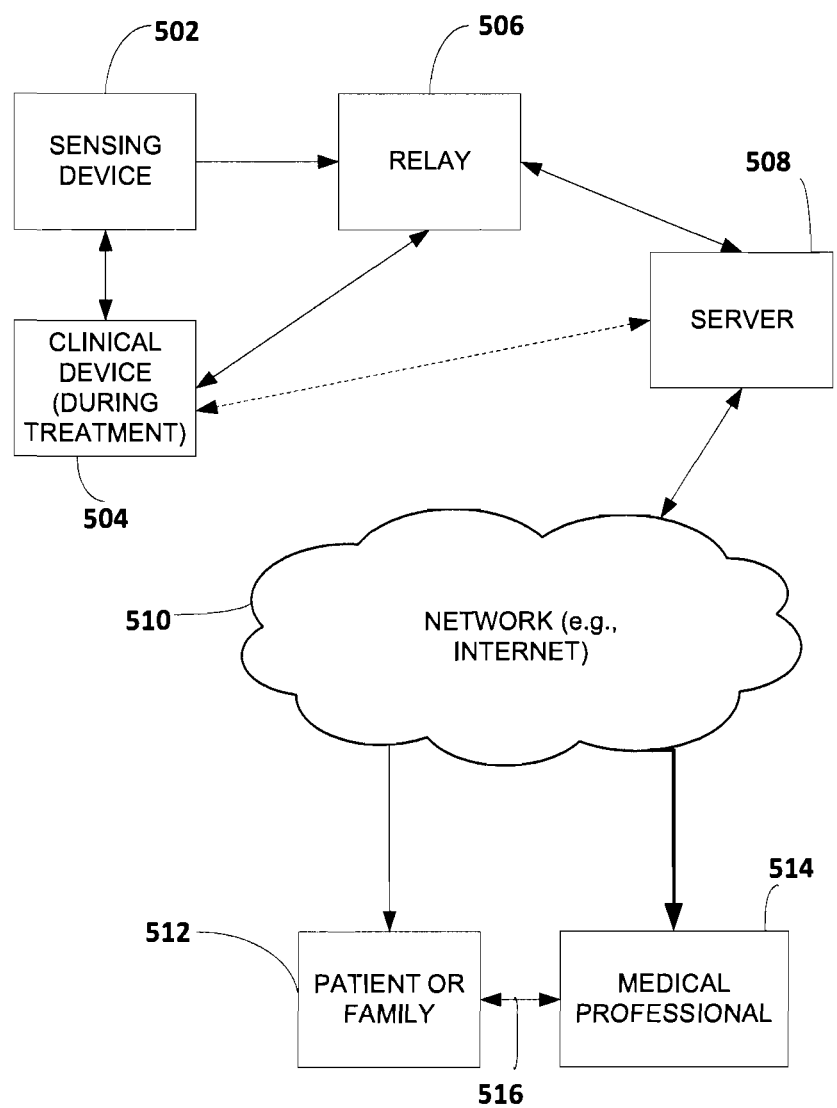
FIG. 5 illustrates a schematic view of a monitoring and reporting system, according to some embodiments.

Referring to FIG. 5, a schematic view 500 of a monitoring and reporting system, according to some embodiments. A sensing medical device 502 may generate signals which are then relayed 506 to a server 508. Alternatively, a clinical device or instrument may generate the signals during a patient treatment, which are then relayed 506 to a server 508. The measurement and analysis of the signals may be performed on-board the device 502 or instrument 504 or performed on the server 508. Alternatively, or in combination, the server 508 may be used to store the analyzed data. The data may be transmitted via a network 510, such as the Internet, an intranet or by phone. A patient 512 may receive the data directly or through a medical professional 514. The information may be passed between the patient 512 and professional 514 for example.

Figure 6:
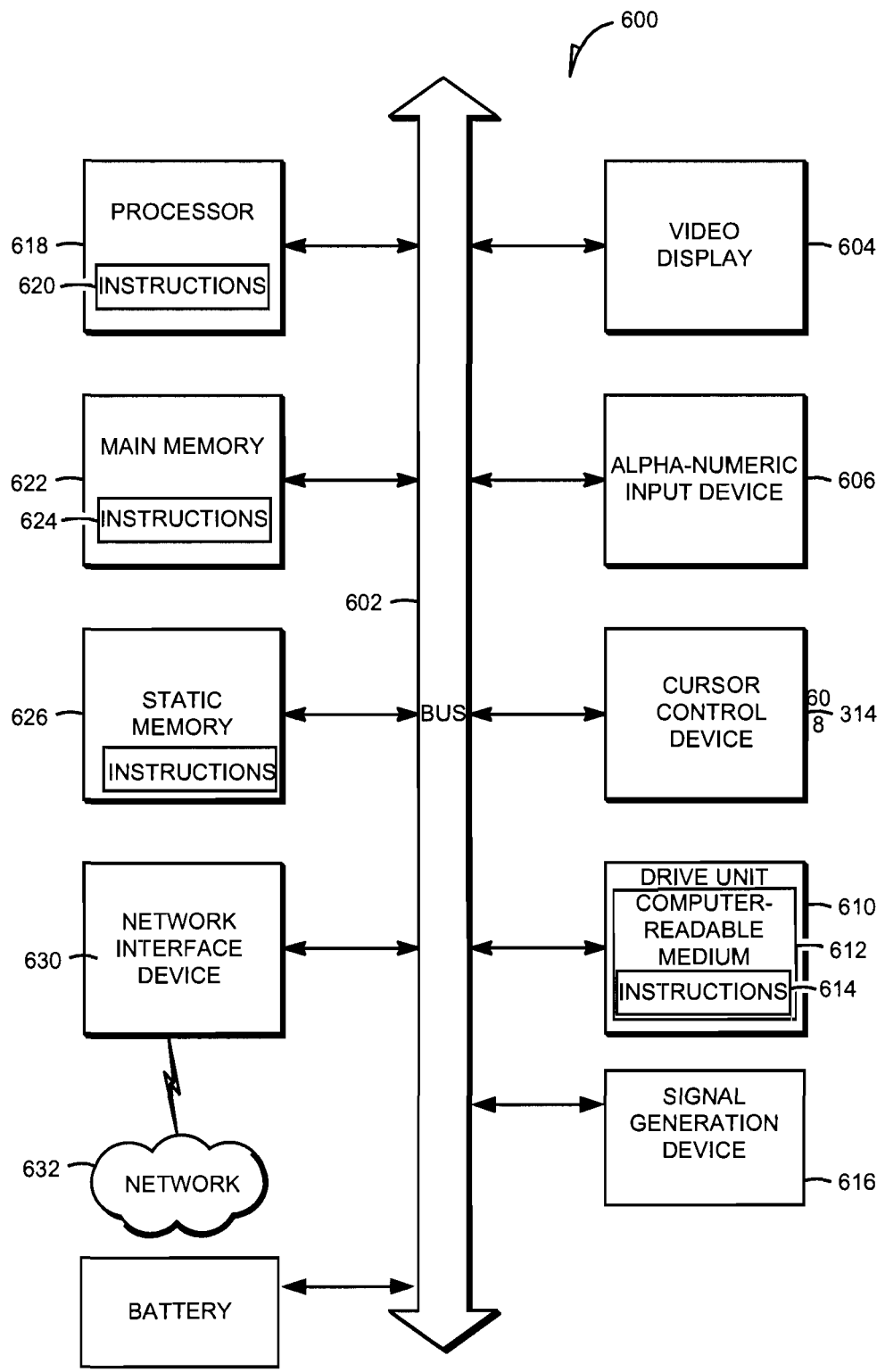
FIG. 6 illustrates a schematic view of medical device and associated system modules, according to some embodiments.

Referring to FIG. 6, a schematic view 600 of medical device and associated system modules, according to some embodiments. FIG. 6 shows an example of the controller within which a set of instructions are be executed causing the device or system to perform any one or more of the methods, processes, operations, or methodologies discussed herein. In an example, the controller can include the functionality of the computer system.

In an example embodiment, the controller operates as a standalone device or may be connected (e.g., networked) to other controllers. In a networked deployment, the one controller can operate in the capacity of a server (master controller) or a client in server-client network environment, or as a peer machine in a peer-to-peer (or distributed) network environment. Further, while only a single controller is illustrated, the term "controller" shall also be taken to include any collection of devices that individually or jointly execute a set (or multiple sets) of instructions to perform any one or more of the methodologies discussed herein.

The example controller includes a processor 618 (e.g., a central processing unit (CPU) or application specific integrated chip (ASIC)), a main memory 622, and a static memory 626, which communicate with each other via a bus 602. The controller can include a video display unit 604 (e.g., a liquid crystal display (LCD) or a cathode ray tube (CRT)). The controller 618 also includes an alphanumeric input device 604 (e.g., a keyboard), a cursor control device 608 (e.g., a mouse), a storage drive unit 610 (disk drive or solid state drive), a signal generation device 616 (e.g., a speaker), and an interface device 630.

The drive unit 610 includes a machine-readable medium 612 on which is stored one or more sets of instructions (e.g., software 614) embodying any one or more of the methodologies or functions described herein. The software 614 can also reside, completely or at least partially, within the main memory 622 and/or within the processor 618 during execution thereof by the controller, the main memory 622 and the processor 618 also constituting machine-readable media. The software 614 can further be transmitted or received over a network 632 via the network interface device 630.

While the machine-readable medium 614 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by a computer or computing device, e.g., controller, or other machine and that cause the machine to perform any one or more of the methodologies shown in the various embodiments of the present invention. The term "machine-readable medium" shall accordingly be taken to include, but not be limited to, solid-state memories, optical and magnetic media, and carrier wave signals.

Figure 7:
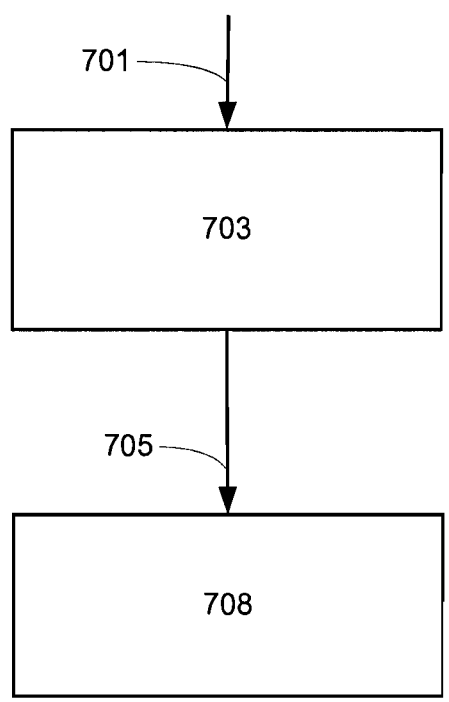
FIG. 7 illustrates a schematic view of a system according to an embodiment of present invention.

Referring to FIG. 7, a schematic view 700 of the process according to an embodiment of the present invention. A plurality of input signals 701 are applied to a patient's body 703, which may or may not change the signal. The first of the input signals 701 can set a base signal. Subsequent input signals can be a pulse train of signals that are separated by a period of time when no input signal is applied from the medical device. The input signals 701 can change in at least one of amplitude, power, or frequency such that the input signals can provoke a response by the patient's body. At least one output signal 705 is sensed from the patient's body 703 in response to the input signal(s) 701. The output signal 705 can be processed in the sensing device 708 or sent to a remote processor by the sensing device 708. In an example, the output signal 705 is compared to the input signal 701. The output signal 705 contains information that is used to indicate physiological data of the patient. In an example, the signal 705 can be attenuated in amplitude relative to the input signal 701 based on the water or fat content of the patient's body. In an example, the signal 705 has a frequency response that is different from the input signal 701 based on the water or fat content of the patient's body. The frequency response can be attenuation in a certain band. The frequency response can be attenuation at a high end of the signal, i.e., the body acts as a low pass filter based on the water or fat content or both of the patient's body. Accordingly, the process view 700 can operate to distinguish fluid, fat, and muscle, or combinations thereof in a patient's body.

Figure 8:
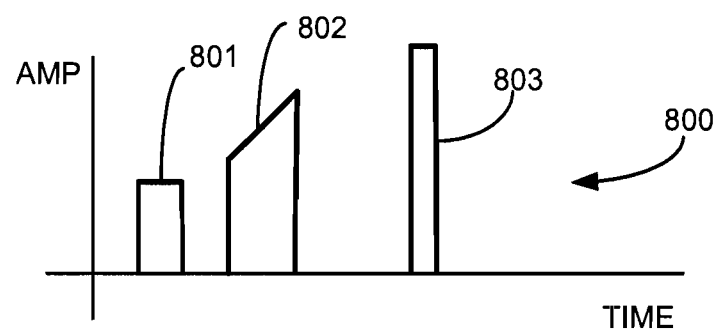
FIG. 8 illustrates a schematic view of signals produces by the devices described herein.

Referring to FIG. 8, a schematic view 800 of a series of signals 801-803 that can be generated by the device 106, 402, 502 or 602. The signals 801, 802, and 803 are each separated from each other in time (x-axis). The signals 801, 802, and 803 each include a frequency component that is not part of the other signals. However, some overlap in frequency can occur in some of the signals applied to the patient. The signals can also include different power or amplitude. These signals are applied to a body of a patient as described herein to produce a signal response that can be sensed by the device(s) 106, 402, 502 or 602.

Figure 9:
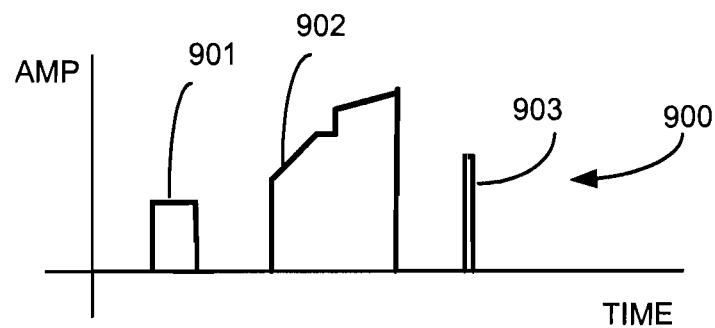
FIG. 9 illustrates a schematic view of signals sensed by the devices described herein.

Referring to FIG. 9, a schematic view 900 of a series of signals 901, 902, and 903 that can be sensed by the device 106, 402 502 or 602 in response to the stimulation signals of FIG. 8. These sensed signals 901, 902, and 903 are the signals that result from the body having the excitation signals applied thereto and the body changing at least one of the excitation signals. The sensed signals 901-903 can be processed using signal processing techniques to produce data that indicates the cardiac status of the patient to whom the signals are applied. The cardiac status of the patient can then be used to individualize treatment for that specific patient and not rely on statistical results to predict the most likely treatment plan as is the currently accepted medical treatment. The cardiac status can include the "wetness", fat, muscle or other cardiac parameters of the patient.

While the above description shows and described three excitation signals 801-803 and three sensed signals 901-903, it will be recognized that these signals could be divided into further subsets of signals and remain within the scope of the present embodiments. The input signals 801-803 and the sensed signals 901-903 need not be equal in number. For example, a single excitation signal 801, 802 or 803 may result in a plurality of sensed signals and, hence, the number of sensed signals can be more than the number of excitation signals.

The medical device as described herein can be used with a system to provide preventative care to a patient that can alert a patient when health care is needed by using the data sensed, derived and/or computed to determine when the patient needs additional medical care based at least in part on the fluid level or fat content of the patient. The present devices are not limited to use in a medical facility and can be worn for extended periods of time outside the medical facility while still accumulating data. This can lower medical costs while assisting in improving the patient outcome.

An example A of the present invention is a medical device that includes a measuring interface, located between a device and a measuring site of a patient, one or more electrodes to generate multiple stimulation frequencies, multiple waveforms or a combination thereof, positioned at the measuring interface and in electrical contact with a portion of the patient, circuitry to measure fluid bioimpedance, fat bioimpedance or a combination thereof, as a result of the generated multiple stimulation frequencies, multiple waveforms or a combination thereof from the one or more electrodes; and a processor system to a isolate fluid contribution and a fat contribution from a total bioimpedance value from which a physiological report can be generated.

An example B include example A above with the measuring interface comprises a patch. An example C can include at least one of example A or B with the circuitry being positioned within the device. An example D can include at least one of examples A-C with the circuitry is positioned remotely from the device. An example E can include at least one of examples A-D with the processor system is positioned within the device. An example F can include at least one of examples A-E with the processor system is positioned remotely from the device.

An example G can include a method of monitoring and analyzing physiological parameters of a patient. The methods includes at least one of electrically connecting one or more electrodes with a measurement site of a patient; generating a stimulation signal or signals, sufficient to provide multiple stimulation frequencies, multiple waveforms or a combination thereof; measuring a one or more bioimpedance values from the generated signals; and analyzing at least one of a fluid bioimpedance contribution, fat bioimpedance contribution or ion bioimpedance contribution within the one or more bioimpedance values, sufficient to generate a physiological report.

An example H can include example G with analyzing comprises isolating. An example I can include example H with generating can include providing an electrical current between two or more of the one or more electrodes. An example J can include H-I and the one or more bioimpedance values comprises a total bioimpedance value. An example K can include any of examples H-J and generating a stimulation signal comprises generating a frequency sweep. An example L can include any of examples H-K and measuring comprises collecting bioimpedance values at specific frequencies. An example M can include any of examples of H-L and collecting bioimpedance values at frequencies correlating to the frequency sweep signals.

An example N can include at least one of examples H-I with the processor system being positioned remotely from the device.

An example O can include performing any of the above methods using the devices of examples A-F.

The Abstract is provided to comply with 37 C.F.R. §1.72 (b), to allow the reader to quickly ascertain the nature of the technical disclosure. It is submitted with the understanding that it will not be used to interpret or limit the scope or meaning of the claims.

The invention claimed is:

1. A medical device, comprising:
   a measuring interface, located between a device and a measuring site of a patient;
   one or more electrodes to generate a frequency sweep stimulation signal, positioned at the measuring interface and in electrical contact with a portion of the patient;
   circuitry to measure total bioimpedance values as a result of the stimulation signal at specific frequencies correlating to the frequency sweep; and
   a processor system to a quantify a fluid contribution, an ion contribution, and a fat contribution from the measured total bioimpedance values from which a physiological report can be generated, wherein the processor system further identifies whether a measured total bioimpendance is reliable based a non-fluid contribution.

2. The medical device of claim 1, wherein the measuring interface comprises a patch.

3. The medical device of claim 1, wherein the circuitry is positioned within the device.

4. The medical device of claim 1, wherein the circuitry is positioned remotely from the device.

5. The medical device of claim 1, wherein the processor system is positioned within the device.

6. The medical device of claim 1, wherein the processor system is positioned remotely from the device.

7. The medical device of claim 1, wherein the processor system further operates to distinguish muscle tissue from either the fat content or the fluid content or both.

8. The medical device of claim 1, wherein the frequency sweep includes a frequency where fat is known to resist an electrical current.

9. The medical device of claim 8, wherein the frequency sweep includes a frequency where fluid is known to interact with an electrical current.

10. The medical device of claim 1, wherein the frequency sweep stimulation signal is between about 5 kHz and about 1000 kHz, between about 100 kHz and about 800 kHz, or 50 kHz and about 500 kHz.

11. The medical device of claim 1, wherein identifying whether a measured total bioimpendance is reliable based a non-fluid contribution includes identifying an un-reliable measurement based on a high ion value.

12. A method of monitoring and analyzing physiological parameters of a patient, comprising:
   electrically connecting one or more electrodes with a measurement site of a patient;
   generating a frequency sweep stimulation signal
   measuring, at the measurement site, total bioimpedance values at specific frequencies correlating to the frequency sweep signal;
   isolating a fluid bioimpedance contribution, fat bioimpedance contribution and ion bioimpedance contribution from the measured total bioimpedance values, sufficient to generate a physiological report; and
   identifying whether a measured total bioimpedance is reliable based a non-fluid contribution.

13. The method of claim 12, wherein generating comprises providing an electrical current between two or more of the one or more electrodes.

14. The method of claim 12, wherein the frequency sweep includes at a frequency where fat is known to resist an electrical current.

15. The method of claim 14, wherein the frequency sweep includes frequency where fluid is known to interact with an electrical current.

16. The method of claim 12, wherein the frequency sweep stimulation signal is between about 5 kHz and about 1000 kHz.

17. The method of claim 12, wherein the frequency sweep stimulation signal is between about 100 kHz and about 800 kHz.

18. The method of claim 12, wherein the frequency sweep stimulation signal is between about 50 kHz and about 500 kHz.

19. The method of claim 12, wherein identifying whether a measured total bioimpendance is reliable based a non-fluid contribution includes identifying an un-reliable measurement based on a high ion value.

20. The method of claim 17, wherein identifying whether a measured total bioimpendance is reliable based a non-fluid contribution includes identifying an un-reliable measurement based on a high ion value.

* * * * *